US011305121B2

(12) United States Patent
Osorio

(10) Patent No.: US 11,305,121 B2
(45) Date of Patent: Apr. 19, 2022

(54) PROGRAMMABLE AUTOTITRATING OF ELECTRICAL PARAMETERS OF IMPLANTABLE MEDICAL DEVICE

(71) Applicant: Flint Hills Scientific, L.L.C., Lawrence, KS (US)

(72) Inventor: Ivan Osorio, Leawood, KS (US)

(73) Assignee: Flint Hills Scientific, LLC., Lawrence, KS (US)

( * ) Notice: Subject to any disclaimer, the term of this patent is extended or adjusted under 35 U.S.C. 154(b) by 122 days.

(21) Appl. No.: 14/203,394

(22) Filed: Mar. 10, 2014

(65) Prior Publication Data
US 2014/0277256 A1   Sep. 18, 2014

Related U.S. Application Data

(60) Provisional application No. 61/799,046, filed on Mar. 15, 2013.

(51) Int. Cl.
*A61N 1/36* (2006.01)
*A61N 1/372* (2006.01)

(52) U.S. Cl.
CPC ..... *A61N 1/36146* (2013.01); *A61N 1/36053* (2013.01); *A61N 1/36064* (2013.01); *A61N 1/36139* (2013.01); *A61N 1/37235* (2013.01); *A61N 1/37247* (2013.01)

(58) Field of Classification Search
CPC ............ A61N 1/08; A61N 2001/36039; A61N 2001/3605; A61N 2001/36064; A61N 2001/36071; A61N 2001/37241; A61N 2001/36128; A61N 2001/36135;
(Continued)

(56) References Cited

U.S. PATENT DOCUMENTS

| 2002/0077670 A1* | 6/2002 | Archer | A61N 1/36064 607/45 |
| 2006/0271108 A1* | 11/2006 | Libbus | A61N 1/36114 607/2 |
| 2008/0051839 A1* | 2/2008 | Libbus et al. | 607/2 |

(Continued)

OTHER PUBLICATIONS

International Patent Application No. PCT/US2014/027111, "International Search Report and Written Opinion of The International Searching Authority," dated Jun. 10, 2014, 11 pages.

*Primary Examiner* — Eugene T Wu
(74) *Attorney, Agent, or Firm* — CF 3; Stephen Eisenmann

(57) ABSTRACT

We report a method of automatically titrating an electrical therapy administered to a patient by an implanted medical device to a target dosage, comprising programming the medical device with a programmed electrical therapy comprising a first target value for a first therapy parameter; programming at least one titration parameter for automatically adjusting the first therapy parameter from a first value to the first target value over a titration time period initiating the electrical therapy, wherein the first therapy parameter comprises said first value; and automatically titrating the electrical therapy by making a plurality of adjustments to the value of the first therapy parameter, whereby the first electrical therapy parameter is changed from the first value to the first target value according to a titration function. We also report a medical device system configured to implement the method.

6 Claims, 9 Drawing Sheets

(58) Field of Classification Search
CPC .......... A61N 2001/36139; A61N 2001/36142; A61N 2001/36146–36178
USPC ................ 607/11, 30, 32, 45, 46, 59, 60
See application file for complete search history.

(56) References Cited

U.S. PATENT DOCUMENTS

| | | | |
|---|---|---|---|
| 2008/0058871 A1* | 3/2008 | Libbus et al. | 607/2 |
| 2010/0106207 A1 | 4/2010 | Dobak, III | |
| 2010/0228314 A1* | 9/2010 | Goetz | 607/41 |
| 2011/0015704 A1* | 1/2011 | Ternes | A61B 5/024 607/62 |
| 2011/0054562 A1* | 3/2011 | Gliner | A61B 5/0484 607/45 |
| 2011/0282416 A1 | 11/2011 | Hamann et al. | |
| 2011/0313488 A1 | 12/2011 | Hincapie Ordonez et al. | |
| 2012/0143286 A1* | 6/2012 | Hahn et al. | 607/59 |
| 2012/0330369 A1* | 12/2012 | Osorio | A61N 1/36139 607/14 |
| 2013/0289646 A1* | 10/2013 | Libbus | A61N 1/36053 607/30 |
| 2013/0289667 A1* | 10/2013 | Wacnik et al. | 607/72 |

\* cited by examiner

PROGRAMMABLE AUTOTITRATING OF ELECTRICAL PARAMETERS OF IMPLANTABLE MEDICAL DEVICE

The present application claims the benefit under 35 U.S.C. § 119(e) of prior-filed provisional application 61/799, 046, filed Mar. 15, 2013, the disclosure of which is hereby incorporated by reference herein.

FIELD OF THE INVENTION

This disclosure relates to medical device systems and methods capable of automated titration of an electrical therapy provided by an implantable medical device (IMD) from a non-therapeutic to a therapeutic dosage. Automated therapy titration as proposed herein may facilitate reaching target dosage levels for electrical therapies provided by IMDs more rapidly, efficiently and cost-effectively than conventional manual programming adjustments that require multiple medical office visits.

SUMMARY OF THE INVENTION

In some embodiments, the present disclosure relates to a method of automatically titrating an electrical therapy administered to a patient by an implanted medical device to a target dosage, comprising: programming the medical device with an electrical therapy, wherein the programmed electrical therapy comprises a first target value for a first electrical therapy parameter defining the electrical therapy; programming at least one titration parameter for automatically adjusting the first electrical therapy parameter from a first value to the first target value over a titration time period of at least two days, wherein the at least one titration parameter is selected from the titration time period, a titration step interval, and a titration step magnitude; initiating the electrical therapy, wherein the first electrical therapy parameter comprises said first value; and automatically titrating the electrical therapy by making a plurality of adjustments to the value of the first electrical therapy parameter, whereby the first electrical therapy parameter is changed from the first value to the first target value according to a titration function.

In some embodiments, the present disclosure relates to a method of automatically titrating an electrical therapy administered to a patient by an implanted medical device to a target dosage, comprising: programming the medical device with an electrical therapy, wherein programming comprises providing a first target value for a first electrical therapy parameter characterizing the electrical therapy; programming at least one titration parameter for automatically adjusting the first electrical therapy parameter from a first value to the first target value over a titration time of at least five days, wherein the at least one titration parameter is selected from the titration time period, a titration step interval, and a titration step magnitude; initiating the electrical therapy, wherein the first electrical therapy parameter comprises said first value; automatically titrating the electrical therapy by making a plurality of adjustments to the value of the at least a first electrical therapy parameter, whereby the first electrical therapy parameter is changed from the first value to the first target value according to a first titration function; receiving a body signal after at least one of said plurality of adjustments to the value of the first electrical therapy parameter; determining whether there is an adverse effect associated with the at least one of said plurality of adjustments, based upon said body signal; returning the value of said first electrical therapy parameter to a prior value to provide a prior electrical therapy program, in response to determining that there is an adverse effect associated with said at least one of said plurality of adjustments; and providing said prior electrical therapy program to said patient. In one embodiment, the adverse effect is selected from discomfort, pain, dyspnea, voice alteration, increased heart rate, and decreased heart rate.

In some embodiments, the present disclosure relates to a medical device system for providing an electrical therapy, comprising: a programmer for programming an implantable medical device with an electrical therapy, wherein the programmer enables a user to program into the medical device a first value for a first electrical therapy parameter characterizing the electrical therapy, a first target value for the first electrical therapy parameter, and at least one titration parameter for automatically adjusting the first electrical therapy parameter from a first value to the first target value over a titration time period of at least two days, wherein the at least one titration parameter is selected from the titration time period, a titration step interval, and a titration step magnitude; an electrode configured to deliver an electrical therapy characterized by a plurality of parameters to a patient; and an implantable medical device, comprising: an electrical therapy module to provide the electrical therapy to the patient using said electrode; and a therapy titration module configured to automatically titrate the electrical therapy by making a plurality of adjustments to the value of the first electrical therapy parameter, whereby the first electrical therapy parameter is changed from the first value to the first target value according to a titration function. In one embodiment, the implantable medical device may comprise a body data module capable of receiving a body signal from the patient, a feedback module configured to provide feedback data to the therapy titration module, wherein the feedback data is based upon one of said body data and a manual input from the patient or a caregiver, and wherein the therapy titration module comprises a dynamic adjustment unit configure to return the value of the first electrical therapy parameter to a previous value after at least a first adjustment, based on said feedback data.

In some embodiments, the present disclosure relates to a non-transitory computer readable program storage unit encoded with instructions that, when executed by a computer, perform a method as described above.

BRIEF DESCRIPTION OF THE DRAWINGS

The disclosure may be understood by reference to the following description taken in conjunction with the accompanying drawings, in which like reference numerals identify like elements, and in which.

Figure 1:
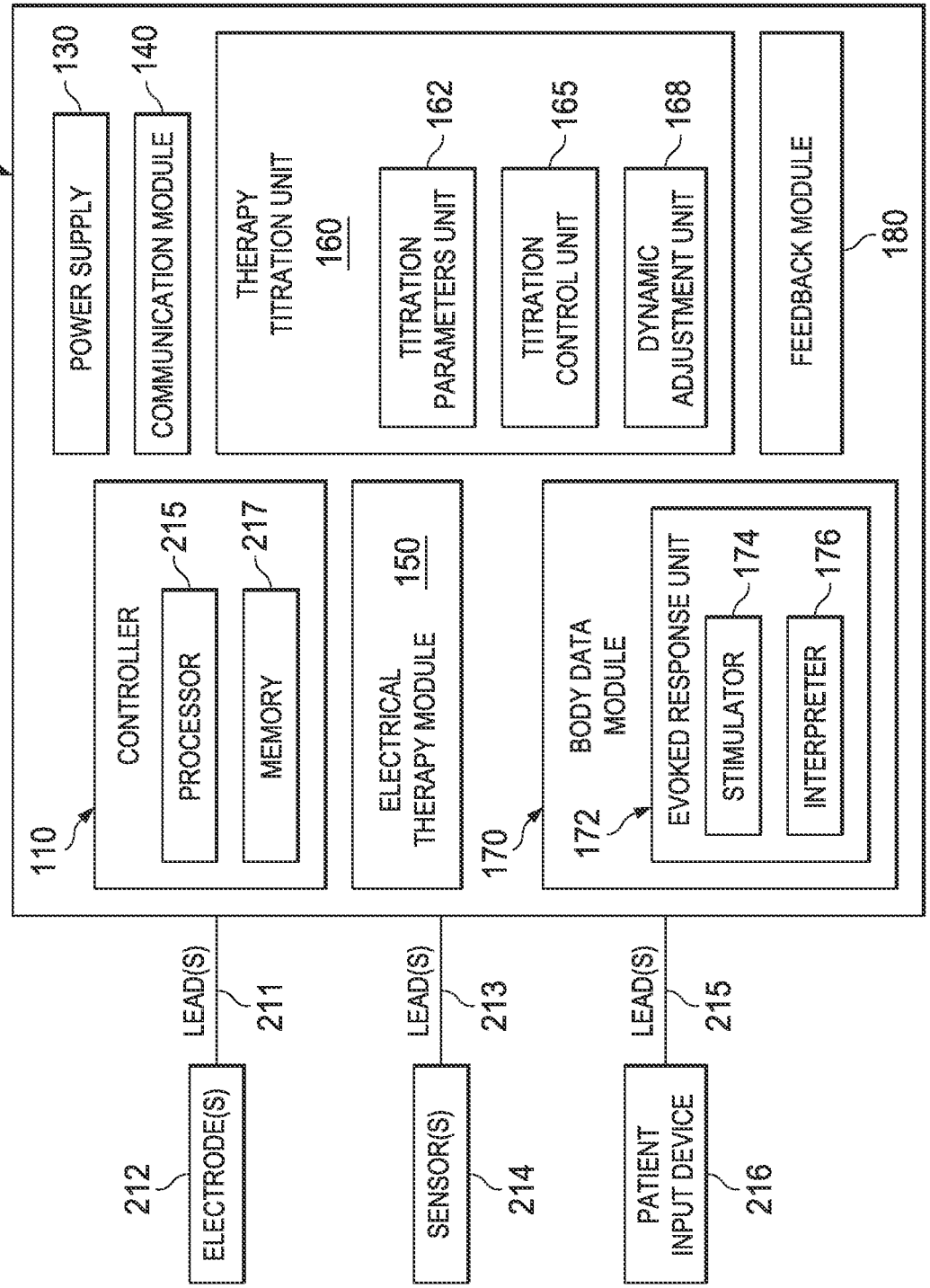
FIG. 1 shows a schematic diagram of a medical device system, in accordance with some embodiments of the present disclosure.

While the disclosure is susceptible to various modifications and alternative forms, specific embodiments thereof have been shown by way of example in the drawings and are herein described in detail. The description herein of specific embodiments is not intended to limit the disclosure to the particular forms disclosed, but on the contrary, the intention is to cover all modifications, equivalents, and alternatives falling within the spirit and scope of the disclosure as defined by the appended claims.

DETAILED DESCRIPTION OF SPECIFIC EMBODIMENTS

Illustrative embodiments of the disclosure are described herein. For clarity, not all features of an actual implementation are described. In the development of any actual embodiment, numerous implementation-specific decisions must be made to achieve design-specific goals, which will vary from one implementation to another. Such a development effort, while possibly complex and time-consuming, would nevertheless be a routine undertaking for persons of ordinary skill in the art having the benefit of this disclosure.

More information regarding automated assessments of disease states, comorbidities, and the like may be found in other patent applications assigned to Flint Hills Scientific, LLC or Cyberonics, Inc., such as, U.S. Ser. No. 12/816,348, filed Jun. 15, 2010; and U.S. Ser. No. 12/816,357, filed Jun. 15, 2010. Each of the patent applications identified in this paragraph is hereby incorporated herein by reference.

More information regarding automated assessments of therapies may be found in other patent applications assigned to Flint Hills Scientific, LLC or Cyberonics, Inc., such as, U.S. Ser. No. 12/729,093, filed Mar. 22, 2010; U.S. Ser. No. 13/280,178, filed Oct. 24, 2011; U.S. Ser. No. 13/308,913, filed Dec. 1, 2011; and U.S. Ser. No. 13/472,365, filed May 15, 2012. Each of the patent applications identified in this paragraph is hereby incorporated herein by reference.

More information regarding the detection of abnormal brain activity, such as seizures, identifying brain locations susceptible to spread of the abnormal brain activity, and treating the susceptible brain locations may be found in other patent applications assigned to Flint Hills Scientific, L.L.C., or Cyberonics, Inc., such as, U.S. Ser. No. 13/449,166, filed Apr. 17, 2012. Any patent application identified in this paragraph is hereby incorporated herein by reference.

More information regarding the detection of brain or body activity using sensors implanted in proximity to the base of the skull may be found in other patent applications assigned to Flint Hills Scientific, L.L.C., or Cyberonics, Inc., such as, U.S. Ser. No. 13/678,339, filed Nov. 15, 2012. Any patent application identified in this paragraph is hereby incorporated herein by reference.

Over the past several decades, medical devices providing electrical therapies to treat a number of medical conditions have been developed and approved. Examples of these therapies include pacing and defibrillation of the heart, electrical stimulation of the spinal cord to treat intractable pain, and stimulation of the vagus nerve to treat epilepsy and depression, among others. In many cases, the patient must be gradually acclimated to the exogenous electrical therapy, and the therapy is gradually increased from a very low dosage to a higher, therapeutically-effective dosage. Heretofore, this process has been performed manually. For example, an epilepsy patient being treated with vagus nerve stimulation may initially be provided with no stimulation for the two weeks following implantation of the device to allow the surgical incision and trauma to heal, after which the physician (or other healthcare provider) may manually program the device to provide a relative low dosage of pulsed electrical therapy, characterized by a current magnitude of 0.1 milliamps (mA)), a pulse width of 0.25 milliseconds, a pulse frequency of 30 Hz, an on-time of 30 seconds, and an off-time of 300 seconds. This initial therapy dosage level may be too low to provide a therapeutic benefit to the patient. Accordingly, the physician may thereafter manually reprogram the patient every 2-4 weeks, to gradually increase the current magnitude in a number of steps to reach a therapeutically-effective, safe, and tolerable dosage level, e.g., from 0.1 mA to 0.5 mA, then to 0.75 mA, 1.0 mA, 1.25 mA, 1.5 mA, 1.75 mA, and finally to 2.0 mA. Such adjustments, referred to herein as therapy titration as the electrical therapy is gradually increased to therapeutically-effective dosage levels, require the patient to make additional office visits at significant cost (in money and time) to both the patient and the treating healthcare provider. The manual titration process may in many cases delay the patient receiving a therapeutic benefit for weeks or months.

Embodiments disclosed herein provide for programming a medical device to implement an electrical therapy following implantation of the device, and to automatically titrate at least one parameter defining the electrical therapy from a first value to a target value. By automatically titrating one or more parameters of the electrical therapy, the patient may be more effectively, more quickly, and more cost-effectively acclimated to the therapy, and may be titrated to a therapeutically-effective dosage of the electrical therapy faster and with less pain and discomfort. The titration may involve increasing or decreasing electrical therapy parameters, and may comprise adjusting one or more parameters (e.g., current (or voltage) amplitude, frequency, pulse width, on-time, off-time, and/or duty cycle) defining the therapy by incremental changes from the first value to the target value. The adjustments to the one or more parameters may be periodic, aperiodic, or contingent. In one embodiment, contingent adjustment refers to an adjustment that is automatically initiated, but which requires a user to respond to a prompt before the adjustment is implemented in the therapy. In one embodiment, changes may be manual or automated or in response to input from a person. In some embodiments, two or more parameters may be automatically titrated from respective first values to respective target values. In some embodiments, undesirable side effects may be detected and used to return one or more automatically titrated parameters to a prior value before resuming the titration to the target value. By using side effects (such as pain, discomfort, or changes in one or more body indices such as heart rate) to indicate a lack of tolerance and/or safety of a particular titration step, titration may be automatically adjusted to rapidly, safely and comfortably titrate the patient to therapeutically-effective, tolerable, and safe therapy dosage levels.

In some embodiments, the medical device may be programmed to establish a first target value for a first electrical therapy parameter. The first electrical therapy parameter may be one or more of the previously noted parameters defining or characterizing the electrical therapy. In some embodiments, the medical device may be programmed to establish a first target value for more than a first electrical therapy parameter, e.g., the device may be programmed to establish first values and/or target values for a first, a second, a third, and an nth electrical therapy parameter. The automated titration of multiple parameters may be sequential, simultaneous, and/or partially overlapping, and may be tailored to address one or more of efficacy, safety, and tolerability, which may be separately impacted by changes associated with each of one or more of the individual parameters.

Embodiments of the invention also involve programming at least one titration parameter for automatically adjusting the first (and/or second, third, etc.) electrical therapy parameter from the first value to the target value. The titration parameter may be selected from a titration time period, a titration step interval, a titration step magnitude, and/or a titration rate. The titration time period is the time period in which an electrical parameter is to be titrated from the initial value to the target value, e.g., 2 weeks. In some embodiments, different titration time periods may be set for each of a plurality of parameters characterizing the electrical signal, e.g., the current may be titrated to the target value over a period of 2 weeks, while the pulse amplitude may be titrated to the target value over one week. The titration step interval is a time interval at which at least one titration adjustment step is made. In some embodiments, all of the titration steps are made at the same titration step interval, while in other embodiments, only the initial titration step interval is provided, and subsequent step intervals are determined based upon a titration function describing how the titration is to occur (e.g., uniformly or non-uniformly). The titration step magnitude is the magnitude of the change made to at least one adjustment of an electrical parameter. For example, current adjustments may be made with a titration step magnitude of 0.1 mA, with each new automatic current adjustment comprising a 0.1 mA increase over the prior value. In some embodiments, titration step magnitudes may be specified for a plurality of electrical parameters (e.g., a current titration step magnitude of 0.1 mA, and a pulse width step magnitude of 0.05 msec). In some embodiments, all of the titration steps for a given electrical parameter are made at the same titration step magnitude, while in other embodiments, only the initial titration step interval is provided, and subsequent step intervals are determined based upon a titration function describing how the titration is to occur (e.g., uniformly or non-uniformly). In one embodiment, the automated titration process may occur at various different scales as a function of titration rate. By way of a first example, the rate at which the target value is reached or approached may be equivalent or comparable to the titration step magnitude divided by the titration time interval. By way of a second example, the rate at which a parameter is changed at a step of the titration.

The titration adjustments may be made according to a titration function describing how the titration steps are to be implemented. In one embodiment, the titration function may be a linear stepwise function in which uniform titration step magnitude changes are made at uniform titration step intervals. In other embodiments, the titration function may be implemented as a non-linear stepwise function, a stepwise approximation of a polynomial, a continuous function, or a mixed stepwise and continuous function. In an example of a non-linear function, one or more of the titration step interval and the titration step magnitude may be non-linear, and may be, for example, a parabolic or higher-order polynomial.

Figure 11:
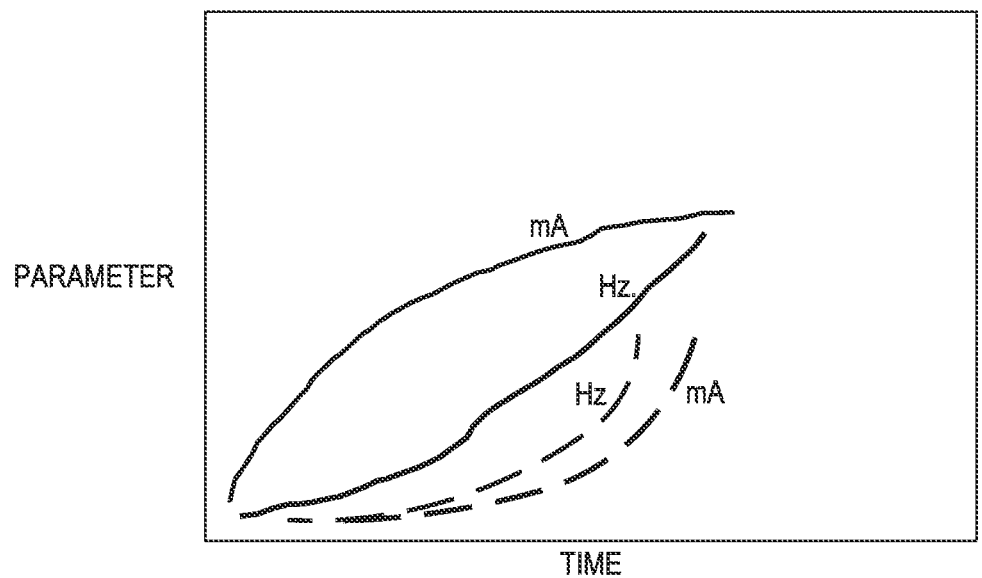
FIG. 11 shows exemplary titration functions for two parameters, according to some embodiments of the present disclosure.
Figure 12:
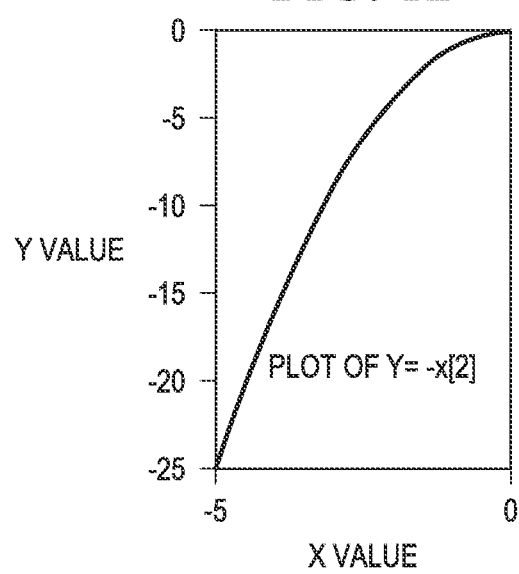
FIG. 12 shows an exemplary titration function, according to some embodiments of the present disclosure.

Non-limiting examples of various titration functions are shown in FIGS. 11-12. FIG. 11 shows that various parameters may vary according to different functions, e.g., for the functions shown in solid lines, the current (in mA) may have a convex shape over the course of the titration, and the frequency (in Hz) may have a concave shape. For another example, for the functions shown in dashed lines, both current and frequency may have the same general shape (e.g., concave) over the course of titration, but one may reach a final value faster than the other. FIG. 12 shows an example of a parabolic function, e.g., $y=-x^2$ for $x=[-5, 0]$.

In some embodiments, a titration function may be self-similar or fractal (i.e., each step may have the same shape as the overall function). Also, although FIGS. 11-12 show smooth parabolic functions, a parabola (or other smooth shape) may be approximated by a series of relatively small steps. As the person of ordinary skill in the art, having the benefit of the present disclosure, will understand, other functions than those shown in FIGS. 11-12 may be used.

The titration function may be programmably selected by a healthcare provider or may be a predetermined function such as a linear function. In some embodiments, the titration function may further be influenced by additional factors such as the patient's age, health status, gender, the severity of the disorder being treated (e.g., seizure type, frequency and severity in patients with epilepsy), the patient's tolerance to adverse events, the patient's tolerance to pain, among other relevant factors.

In some embodiments, the titration function may be interrupted or modified by the occurrence of one or more events, such as one or more side effects, patient tolerance, patient safety, or patient disease state, among others. For example, the titration function as initially programmed may be automatically adjusted to accelerate, slow down, or temporarily suspend or reverse the titration process based upon one or more body signal(s). The one or more body signals may be analyzed by the medical device and an automated adjustment of the titration process may be performed by, e.g., lowering a parameter value that results in undesired side effects such as discomfort, pain, respiratory effects (e.g., dyspnea), voice alteration, changes in heart rate, etc., to allow the patient additional time to accommodate to the previous stimulation dosage before resuming the titration process. In addition, feedback from external sources, e.g., manual input by the patient or a caregiver may, also be used to reverse, slow down, or accelerate the titrating of the therapy.

The titration of the therapy may be implemented by initiating the electrical therapy with the one or more parameters to be titrated set at their respective initial values. The therapy may thereafter be titrated by automatically adjusting the one or more electrical therapy parameters based upon the programmed one or more titration parameters (e.g., the titration time period, titration step period, titration step magnitude, and/or titration rate) and the titration function.

As an example, a health care provider may program a medical device to provide an electrical therapy in which a first parameter such as electrical pulse current increases from an initial value of 0 mA to a target value of 2.0 mA. The therapy may be automatically titrated from the initial value to the target value based on the titration time period according to the titration function. In one embodiment, various steps between the initial value and the target value may be made such that the titration process causes the therapy signal to have a specific value at each of these intermediate steps until the target value is achieved. That is, the automatic titration feature may "ramp up" a parameter defining the electrical therapy by increasing the parameter in small increments over a programmed titration time period. In a particular embodiment, the incremental increase may be implemented once each day over a programmed time period selected from one day to 60 days, and may include two days, three days, four days, five days, one week, ten days, two weeks, three weeks, four weeks, or any other period from 2-60 days. In one embodiment, titration may be adjusted in view of one or more of patient input, body signals, or brain evoked responses.

In some embodiments, a user may not need to explicitly program a titration time period. Instead, the user may program a titration step magnitude and a titration step interval. According to such embodiments, the electrical therapy is initiated with the therapy parameter at a first value, and the value is iteratively increased by the titration step magnitude after the lapse of each titration step interval. For example, an electrical therapy used to provide vagus nerve stimulation therapy to a patient may be increased by 0.1 mA (or other titration step magnitude) each day (or other titration step interval) until the target value is reached. The patient, physician or healthcare provider may be sent a message when the target dosage is reached according to some embodiments.

In other embodiments, the titration of the therapy may be automatically or manually altered. For example, in some embodiments, body data from the patient may be used to evaluate one or more effects of the automatic therapy titration. Based on the one or more effects of the therapy, the titration of the therapy may be altered. In another embodiment, if efficacy is detected (as determined, e.g., from body data) during the titration process, then further titrating of the therapy may be suspended. Alternatively, if side effects of the therapy are found, the titration may be suspended or reversed until further interaction with a healthcare provider. In some embodiments, the titration process may be reversed upon a first detection of a side effect, and after resuming the titration process, detection of a second or a third side effect may result in suspension of further automatic titration of the electrical therapy until the patient's physician programs the medical device to resume the titration, in which case an alert may be sent to the physician or other caregiver. In a further embodiment, if no adverse effects of the therapy are noted, the titration of the therapy may be accelerated to reach the target value sooner than a programmed titration time period. The adjustment of the titrating process may be an automated iterative process, wherein adjustments to the titrating steps may be altered based upon body data analysis during each delivery of therapy.

FIG. 1 shows a stylized block diagram representation of a medical device system, according to some embodiments of the present disclosure. The medical device system 50 may comprise a medical device 100, electrode(s) 212, lead(s) 211 coupling the electrode(s) 212 to the medical device 100, sensor(s) 214, and lead(s) 213 coupling the sensor(s) 214 to the medical device 100. The electrode(s) 212 may be configured to deliver an electrical therapy defined by a plurality of parameters to a patient. The sensor(s) 214 may be configured to collect body data relating to any body data stream of the patient, which may include as non-limiting examples one or more of the patient's cardiac signal (e.g., heart rate, heart rate variability), respiratory signal (e.g., respiratory rate, end tidal volume, respiratory rate variability), blood oxygen saturation, blood oxygen saturation variability, discomfort level, gastro-intestinal activity, shortness of breath, or vocal cord function. The medical device system 50 includes a programmer 250 which may be used to program the medical device 100, which in some embodiments is an implantable medical device (IMD), a partially implantable medical device, or a portable external medical device with one or more parameters characterizing the electrical therapy and one or more titration parameters to automatically titrate the one or more parameters from a first value to a target value. In some embodiments, a patient (manual) input device 216 may be coupled to the medical device 100 by lead(s) 215 or by a wireless coupling (not shown), and may be used to provide an input (which may be a manual input or an automatic input from, e.g., an accelerometer other sensing device incorporated in the patient input device 216) from the patient.

Various components of the medical device 100, such as controller 120, processor 115, memory 117, power supply 130, and communication unit 140 have been described in other patent applications assigned to Flint Hills Scientific, LLC or Cyberonics, Inc., such as, U.S. Ser. No. 12/770,562, filed Apr. 29, 2010; U.S. Ser. No. 12/771,727, filed Apr. 30, 2010; U.S. Ser. No. 12/771,783, filed Apr. 30, 2010; U.S. Ser. No. 12/884,051, filed Sep. 16, 2010; U.S. Ser. No. 13/554,367, filed Jul. 20, 2012; U.S. Ser. No. 13/554,694, filed Jul. 20, 2012; U.S. Ser. No. 13/559,116, filed Jul. 26, 2012; and U.S. Ser. No. 13/598,339, filed Aug. 29, 2012; U.S. Ser. No. 12/896,525, filed Oct. 1, 2010, now U.S. Pat. No. 8,337,404, issued Dec. 25, 2012; U.S. Ser. No. 13/098, 262, filed Apr. 29, 2011; U.S. Ser. No. 13/288,886, filed Nov. 3, 2011; U.S. Ser. No. 13/554,367, filed Jul. 20, 2012; U.S. Ser. No. 13/554,694, filed Jul. 20, 2012; U.S. Ser. No. 13/559,116, filed Jul. 26, 2012; and U.S. Ser. No. 13/598, 339, filed Aug. 29, 2012. Each of the patent applications identified in this paragraph is hereby incorporated herein by reference.

The medical device 100 may comprise an electrical therapy module 150 to generate an electrical therapy signal that may be provided as an electrical therapy to a target body structure such as a cranial nerve or brain tissue via electrodes 212. The electrical therapy signal may be characterized by a plurality of parameters, e.g., an amplitude, a pulse width, a pulse frequency, a signal on-time, or a signal off-time, among others. The electrical therapy module 150 may be configured to deliver an electrical therapy signal having a low initial or first value of one or more parameters upon initiation of the treatment regimen. The treatment regimen may be initiated after implantation of electrode(s) 212, medical device 100, or other components of the medical device system 50. Alternatively or in addition, the therapy may be initiated as part of a "reboot" or "reset" of a previously suspended therapy. In one embodiment, the electrical therapy signal may be programmed along with one or more titration parameters to titrate an electrical current setting for electrical pulses applied to a target structure from a first value (e.g., 0 mA or 0.1 mA) to a target value for providing therapy (e.g., 2.5 mA).

The treatment regimen may be configured to treat epilepsy, depression, pain, congestive heart failure, traumatic brain injury, or obesity, among other ailments known to persons of skill in the art to be amenable to treatment by electrical therapy of the body, e.g., of neural structures, e.g., of the brain, spinal cord, or a cranial nerve, e.g., the vagus nerve.

Figure 2:
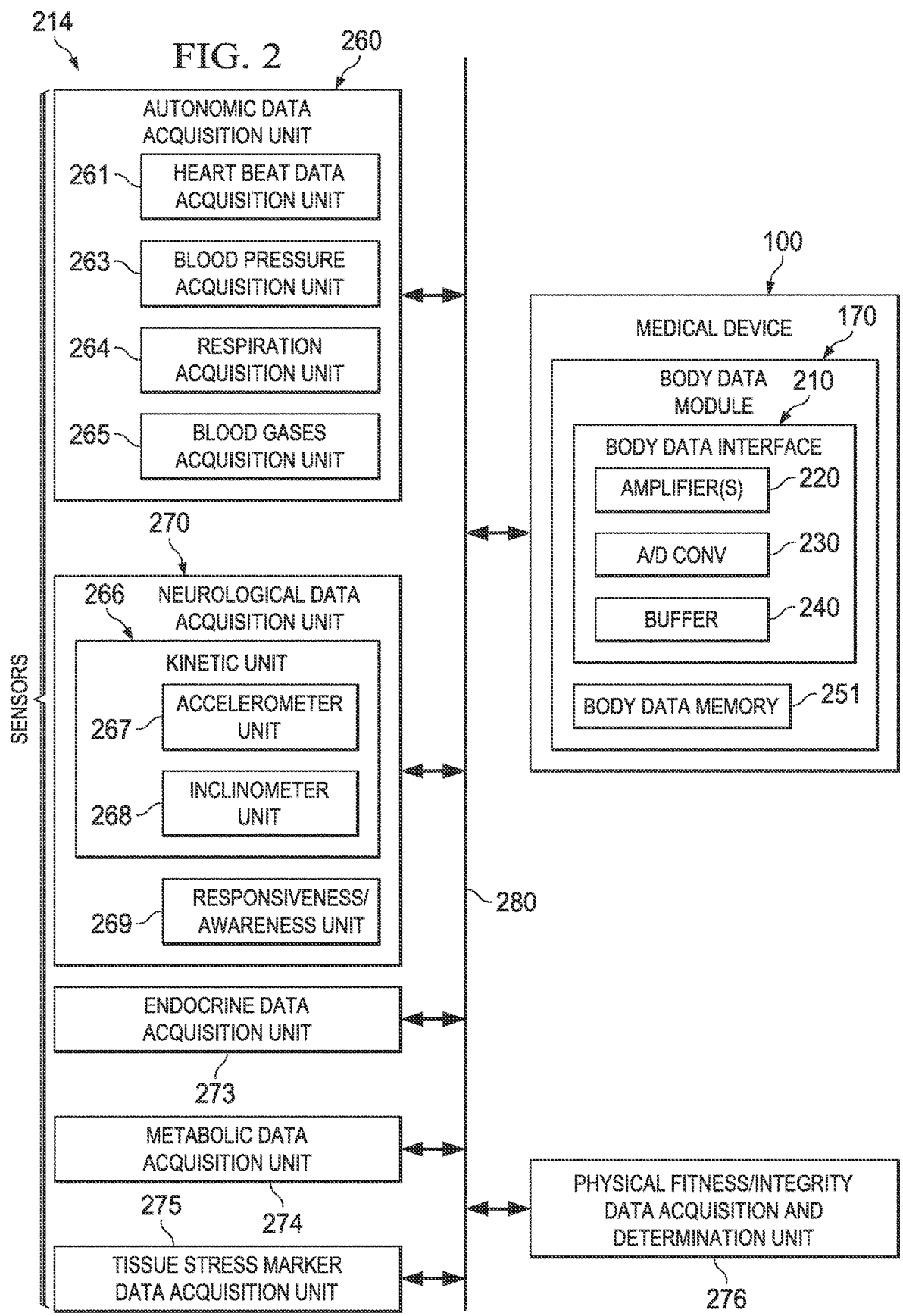
FIG. 2 shows a schematic diagram of data acquisition components of a medical device system, in accordance with some embodiments of the present disclosure.

The medical device 100 may also comprise a body data module 170. The body data module 170 is capable of acquiring signal(s) relating to a patient's body data, processing and analyzing the signals to assess the effects (beneficial or deleterious) of the therapy on the patient. The body data module 170 may also be configured to determine one of a time series of body data values or body index values based upon the time series. Such a time series of body index values may comprise at least one of an instantaneous heart rate (HR), a heart rate variability (HRV), an instantaneous respiratory rate (RR), an instantaneous blood pressure (BP), an instantaneous blood oxygen saturation (O2S) value, a blood oxygen saturation variability, or vocal cord function, among others. Body data module 170 is shown in FIG. 2 and accompanying description below.

In one embodiment, the body data module 170 may comprise an evoked response unit 172. The evoked response unit 172 may be configured to apply a signal to a body tissue and determine what response, if any, is evoked in the tissue by the signal. For example, the evoked response unit 172 may comprise a stimulator 174 configured to apply a signal expected to evoke a response, and an interpreter 176 configured to determine what response, if any, was evoked by the signal.

In one embodiment, the evoked response unit 172 may be a vagus evoked response unit, i.e., a unit configured to acquire data from the vagus nerve relating to responses evoked on a body tissue (e.g., a vagus nerve, a heart, or a brain or a region thereof) by an electrical stimulation or to acquire EEG or ECoG data. Alternatively or in addition, the evoked response unit 172 may be a voice evoked response unit, i.e., a unit configured to acquire data from the patient's body relating to responses evoked on the vocal cords and/or other vocal apparatus by an electrical stimulation or other therapy modality. For example, vagus nerve stimulation may interfere with a patient's vocal cord function, e.g., by rendering the voice hoarse or husky, and an evoked response unit 172 according to this embodiment may gather and analyze data relating to such evoked responses.

The medical device 100 may comprise a therapy titration module 160 configured to titrate one or more electrical therapy parameters to a target value according to a titration function. The titration may involve decreasing the therapy parameters at certain times in response to the occurrence of an adverse event. (As used herein, "adverse event" refers to side effects and/or other undesirable events). In some embodiments, the titration is continued until one or more of a tolerable, a safe, an efficacious, and/or a target electrical parameter value is achieved. In other words, the target dosage may be either tolerable, efficacious or both. In some embodiments, the programmed target value for a titration parameter may be altered to a lower or higher value based upon one or more of a measured level of efficacy (or lack of efficacy) or the emergence of side effects.

The titration module 160 may comprise a titration control unit 165 configured to determine and implement the titration function. In some embodiments, the titration function may be determined by looking up information from a titration parameter module 162. In some embodiments, titration parameters for performing the titration may also be programmed into the medical device 100 from an external programming device 250 by a physician, and stored into memory. The titration parameters may include one or more of the titration time period, the titration step interval, the titration step magnitude, the titration rate, and one or more other parameters defining the titration function.

Figure 3:
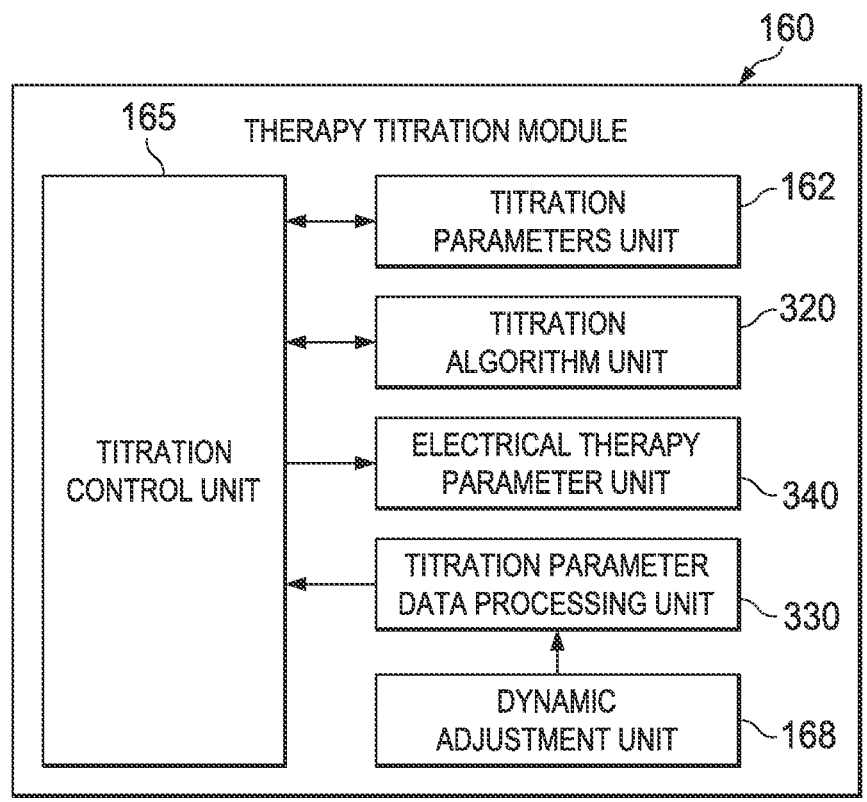
FIG. 3 shows a schematic diagram of a therapy titration module, according to some embodiments of the present disclosure.

As shown in FIG. 3, in some embodiments, the therapy titration module 160 may comprise a titration parameter data processing unit 330 to process data to implement the titration of the one or more electrical therapy parameters; a titration algorithm unit 320 for providing instructions relating to titrating of one or more electrical parameters of the electrical therapy signal; the titration control unit 165 to receive data from at least one of the titration parameter data processing unit 330, the titration algorithm unit 320, and the titration parameters unit 162. Therapy titration unit 160 may further comprise an electrical therapy parameter unit 340, operatively coupled to the titration control unit 165, to provide one or more values of the electrical therapy parameters to be titrated to the electrical therapy module 150, such as one or more initial (or first) and target values for the electrical parameters to be titrated, as well as values for other parameter that are not intended to be titrated. In some embodiments, the titration parameter data processing unit 330 may be configured to receive data from a dynamic adjustment unit 168, described below. The titration parameter data processing unit 330 may be capable of processing data to determine a titration protocol or function. The titration function may be defined by one or more parameters that determine how the electrical therapy parameters are to be titrated to the target value and may determine one or more titration periods, titration step intervals, titration step magnitudes, and/or titration step rates.

The therapy titration module 160 may further comprise a dynamic adjustment unit 168 configured to adjust one or more electrical parameters and/or titration parameters based on the feedback data from, e.g., sensors 214 and/or feedback module 180. The dynamic adjustment unit 168 may accelerate, slow down, suspend, or resume the programmed titration process according to body data received from the patient. In some embodiments, the dynamic adjustment unit 168 may be used to determine one or more of a measure of efficacy of the therapy (to identify and/or quantify whether or not the electrical therapy is efficacious) or a side effect of the therapy, and to use such measure of efficacy, lack of efficacy, or side effects, to cause titration control unit 165 to accelerate, interrupt or suspend, reduce, or resume the therapy titration process. In some embodiments, the dynamic adjustment unit 168 may cause titration control unit 165 to adjust the one or more electrical therapy parameters to slow the titration of the one or more electrical therapy parameters to their respective target values, while in others the titration function may be adjusted to speed up the titration to the target value. For example, if the feedback data indicates that the patient suffered an adverse reaction to the electrical therapy, the dynamic adjustment unit 168 may increase the titration step interval to slow titration of the electrical therapy parameter(s), or it may reduce one or more electrical therapy parameters being titrated to the most recent value not associated with an adverse effect. Doing so may eliminate or reduce a side effect, and allow the patient additional time to accommodate to a particular titration step. As another example, if the feedback data indicates that the patient did not suffer an adverse reaction to the treatment and the treatment lacks sufficient efficacy, the dynamic adjustment unit 168 may reduce a titration step interval to prompt a faster titration of the therapy. In this manner, the dynamic adjustment unit 168 and the therapy titration module 160 are capable of improving safety and efficacy of therapy.

Returning to FIG. 1, the medical device 100 may comprise a feedback module 180 configured to provide feedback data from the patient's body, wherein the feedback comprises at least one of body data (e.g., that provided by body data module 170) or a manual input from the patient (e.g., provided by patient input device 216). The feedback module 180 may provide feedback relating to the efficacy of the treatment, the safety of the treatment, one or more body reactions to the treatment, etc. The feedback module 180 may also provide external feedback received from the patient or a medical professional. Information from the feedback module 180 may be used to adjust the titration of the therapy.

Figure 4:
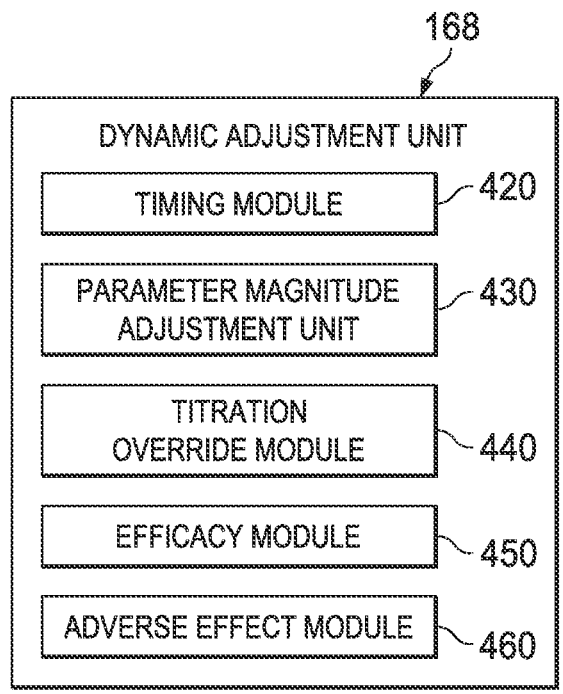
FIG. 4 shows a schematic diagram of a dynamic adjustment unit, according to some embodiments of the present disclosure.

Turning now to FIG. 4, the dynamic adjustment unit 168 may also comprise a parameter magnitude adjustment unit 430, a timing module 420, an efficacy module 450, an adverse effect module 460, and a titration override module 440. The parameter magnitude adjustment unit 430 may be configured to provide data relating to the magnitude of one or more adjustments to be made to the value of an electrical therapy parameter. The timing module 420 may be configured for determining the timing of one or more adjustments to be made to the value of an electrical therapy parameter to be titrated (e.g., the length of time the electrical parameter is kept at a particular value, and/or the times at which the parameter is adjusted to a next value or a previous value). Data from the parameter magnitude adjustment unit 430 may be utilized by the timing module 420 to determine the timing of the adjustments to the electrical therapy parameters.

The adverse effect module 460 (which may also be referred to as a side effect module) may be configured to determine at least one adverse effect of the electrical therapy, e.g., an observation that the treatment regimen is unsafe and/or intolerable. Data from the adverse effect module 460 may be used by the parameter magnitude adjustment unit 430 and/or timing module 420 to determine the rate of increase for titrating one or more parameters of the electrical therapy signal. For example, if the adverse effect module detects that certain parameter values of the electrical signal, at a certain point in the therapy titration process, cause an adverse event (e.g., pain, vocal problems, sudden drop in blood pressure or heart rate, etc.), the parameter magnitude adjustment unit 430 may reduce the rate of increase of an electrical therapy parameter, maintain the current value of the parameter, or may reduce the value of the parameter, to allow the adverse event to resolve. In some embodiments, these actions may be taken for more than one electrical therapy parameter. Further, the adverse effect module 460 may correlate certain titration adjustments to adverse effects and store such data. This data may be used by medical device 100 to control parameters of future titrations.

In one embodiment, the dynamic adjustment unit 168 may include an efficacy module 450 configured to determine at least one body index comprising a measure of efficacy of the electrical therapy. The efficacy index may be determined based at least in part on collected body data or on reports or input from the patient. In some embodiments, the dynamic adjustment unit 168 may be configured to adjust the value of an electrical parameter to be titrated based on the one or more efficacy index values. Depending upon whether the efficacy module 450 indicates that the therapy is efficacious, not efficacious, or is indeterminate, the titration process may be modified (e.g., accelerated, interrupted or suspended, or reversed, among others). More particularly, data from the efficacy module 450 regarding the efficacy of the electrical therapy may be used by the parameter magnitude adjustment unit 430 to make automated adjustments to the titration parameter(s), and/or by the timing module 420 to change the timing of the adjustments to the parameter(s). As a non-limiting example, if the efficacy data indicates that the previously applied treatment was not sufficiently efficacious within a predetermined time period, the electrical therapy signal may be changed by increasing the magnitude of the adjustment to be made to an electrical therapy parameter, and/or decreasing the time period required before the next adjustment is made, in an effort to increase the electrical therapy dosage provided to the patient. In alternative embodiments, the efficacy module 450 may instead be a component of another portion of the medical device 100 rather than the dynamic adjustment unit 168.

The term "reduce" the value of the electrical parameter is used above in view of the typical situation where the titration of the electrical parameter is from a low initial value to a high target value associated (or expected to be associated) with efficacy. This is generally the case for amplitude, pulse width, and pulse frequency. An adverse effect may result from a titration with too high a step magnitude or step rate, or with a step implemented too soon (i.e., with a step interval that is too short) for the patient to have acclimated to a prior titration increase. In such cases, reducing the value may be appropriate to minimize or reverse the adverse effect. However, some parameters, e.g., signal off-time, may be titrated from a high initial value to a low target value associated with efficacy. In such situations, increasing the value of the signal off-time may be appropriate to minimize or reverse the adverse effect, and to allow the patient a longer period of time to become habituated or acclimated to a particular titration increase.

The dynamic adjustment unit 168 may also comprise a titration override module 440 for overriding the programmed titration of the electrical therapy parameter(s). For example, based upon a signal from the adverse effect module or an input from the patient or a healthcare provider, the titration override module 440 may override the programmed titration. The overriding of the titration may include suspending a next planned adjustment to the one or more electrical therapy parameters being titrated. Subsequent adjustments to the electrical therapy parameter(s) may be provided according to data generated by one or more of timing module 420, the parameter magnitude adjustment unit 430, efficacy module 450, and adverse effect module 460. The subsequent adjustments may include stopping a current titration process and implementing a default titration process, ending the titration process altogether, implementing a slower titration process, implementing titration to a higher (or lower) final value, etc.

FIG. 2 shows a block diagram depiction of a medical device 100, in accordance with one illustrative embodiment of the present invention. FIG. 2 depicts an exemplary implementation of the body data module 170 described above with respect to FIG. 1. The body data module 170 may include a body data memory 251 for storing and/or buffering data in the body data module 170. The body data memory 251 may, in some embodiments, be adapted to store body data for logging or reporting purposes and/or for future body data processing. The body data module 170 may also include one or more body data interfaces 210. The body data interface 210 may provide an interface for input/output (I/O) communications between the body data module 170 and body data units/modules (e.g., [260-270], [273-276]) via connection 280. Connection 280 may a wired or wireless connection, or a combination of the two. The connection 280 may be a bus-like implementation or may include an individual connection (not shown) for each or some number, of the body data unit (e.g., [260-270], [273-276]). The connection 280 may also include connection elements as would be known to one of skill in the art having the benefit of this disclosure. The specific implementation of the connection 280 does not serve to limit other aspects of various embodiments described herein unless specifically described. In this regard, body data acquisition units/modules 260, 270, 273, 274, 275 may also include one or more of sensors 214 and leads 215 (FIG. 1).

In various embodiments, the body data units may include, but are not limited to, an autonomic data acquisition unit 260, a neurologic data acquisition unit 270, and endocrine data acquisition unit 273, a metabolic data acquisition unit 274 and/or a tissue stress marker data acquisition unit 275. In one embodiment, the body data units may include a physical fitness determination unit 276. In one embodiment, the autonomic data acquisition unit 260 may include a heart beat data acquisition unit 261 adapted to acquire heart sounds, EKG data, PKG data, heart echo, apexcardiography and/or the like, a blood pressure acquisition unit 263, a respiration acquisition unit 264, a blood gases acquisition unit 265, and/or the like. In one embodiment, the neurologic data acquisition unit 270 may contain a kinetic unit 266 that may comprise an accelerometer unit 267, an inclinometer unit 268, and/or the like; the neurologic data acquisition unit 270 may also contain a responsiveness/awareness unit 269 that may be used to determine a patient's responsiveness to testing/stimuli and/or a patient's awareness of their surroundings. These lists are not inclusive, and the body data module 170 may collect additional data not listed herein, that would become apparent to one of skill in the art having the benefit of this disclosure. The body data acquisition units ([260-270], [273-276]) may be adapted to collect, acquire, receive and/or transmit heart beat data, EKG data, PKG data, heart echo, apexcardiography, heart sound data, blood pressure data, respiration data, blood gases data, body acceleration data, body incline data and/or the like.

The body data interface(s) 210 may include various amplifier(s) 220, one or more A/D converters 230 and/or one or more buffers 240 or other memory (not shown). In one embodiment, the amplifier(s) 220 may be adapted to boost incoming and/or outgoing signal strengths for signals such as those to/from any body data units/modules (e.g., ([260-270], [273-276]) or signals to/from other units/modules of the IMD 200. The A/D converter(s) 230 may be adapted to convert analog input signals from body data unit(s)/module(s) (e.g., ([260-270], [273-276]) into a digital signal format for processing by controller 210 (and/or processor 215). Such analog signals may include, but is not limited to, heart beat data, EKG data, PKG data, heart echo, apexcardiography, heart sound data, blood pressure data, respiration data, blood gases data, body acceleration data, body incline data and/or the like. A converted signal may also be stored in a buffer(s) 240, a body data memory 251, or some other memory internal to the IMD 200 (e.g., memory 217) or external to the IMD 100 (e.g., patient input device 216 or programmer 250). The buffer(s) 240 may be adapted to buffer and/or store signals received by the body data module 170 as well as signals to be transmitted by the body data module 170. In various embodiments, the buffer(s) 240 may also be adapted to buffer and/or store signals in the body data module 170 as these signals are transmitted between components of the body data module 170.

Figure 5:
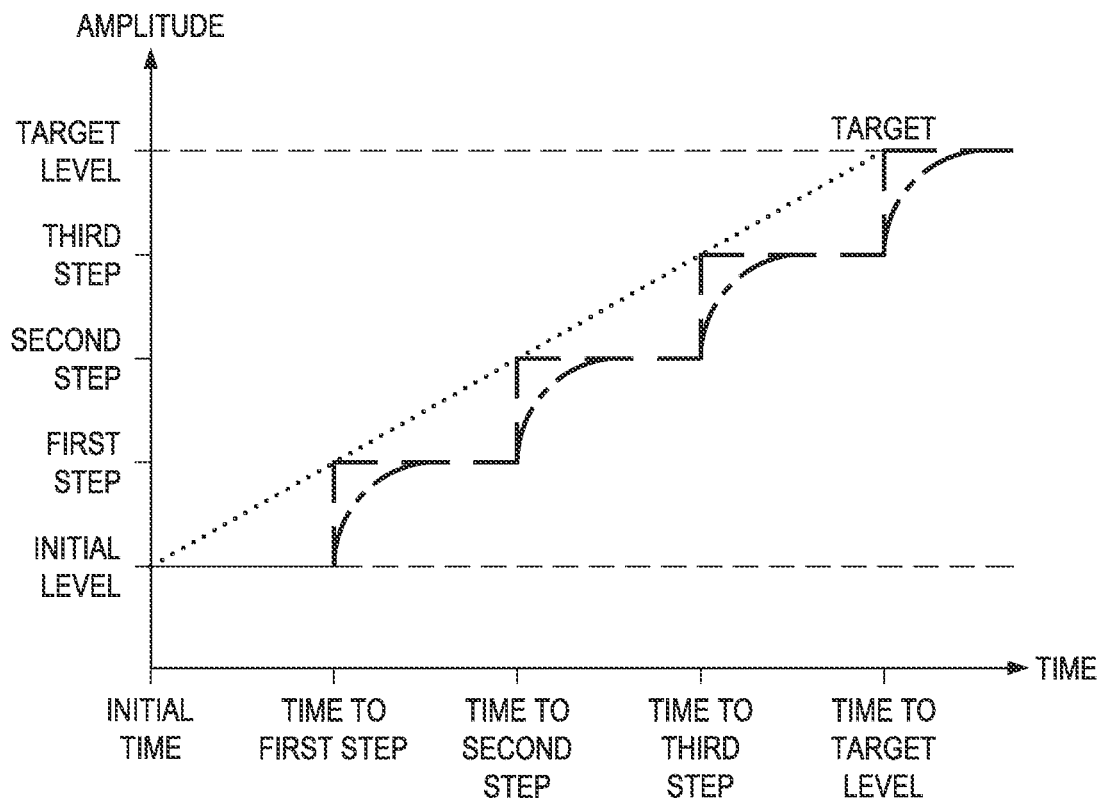
FIG. 5 shows an example of a titration comprising a series of increasing adjustments to a first electrical parameter from a first value to a first target value, according to some embodiments of the present disclosure.

FIG. 5 depicts a stylized depiction of one example of a titration of an electrical therapy, according to some embodiments herein. In one embodiment, the illustration in FIG. 5 may represent a titration of a first electrical therapy parameter, e.g., the current amplitude of the therapy signal. In alternative embodiments, the illustration of FIG. 5 may represent a titration of a plurality of parameters, e.g., a composite representation of amplitude and pulse width or frequency. Additional but different figures, having different timing and magnitude for the adjustments, could be provided for a second, third, fourth, etc., parameter to be titrated. Those skilled in the art having benefit of the present disclosure would appreciate that the general principles of FIG. 5 are applicable to any electrical parameter that may be part of a titration of an electrical therapy of a patient by adjusting the parameter from a first value to a target value.

Starting from a first or initial magnitude shown in FIG. 5, the first electrical therapy parameter may be increased by a titration step magnitude (dashed line shown in FIG. 5 as being the same for each step but which may be different in alternative embodiments) at each of a plurality of titration step intervals (also depicted as uniform in FIG. 5 but which may be different in alternative embodiments. The period from the initial time (when the therapy is started) to the time at which the target value is reached is the titration time period. From the initial time to $1^{st}$ step, the electrical therapy parameter remains at the first value to allow the patient's body to be acclimated to the therapy signal at the first value. At the first step, the first parameter value is increased to a second, higher value (e.g., from 0.1 to 0.2 mA), and it remains at that value for the titration step interval, at the lapse of which the first parameter value is then increased (at the $2^{nd}$ step) to a 3rd, still higher value. The first parameter remains at the 3rd value for another titration step interval, at which time (the $3^{rd}$ step), when the value is raised to a $4^{th}$ value. After the lapse of another titration step interval, the first parameter is then increased (at the $4^{th}$ step) to the target value. The representative process illustrated may be made in a greater number of steps with smaller titration step magnitudes to improve the patient's ability to tolerate each step. The stepwise process is repeated until the target value of the first parameter is reached. The time to target value may be determined by the timing module 420 (FIG. 4) of the dynamic adjustment module 170.

FIG. 5 also shows the titration rate on two timescales, e.g., a global time scale (dotted line), comparable in value to the sum of the titration step magnitudes divided by the time to target level, and local time scales (dashed and dashed-dotted lines), indicating alternative approaches to bringing the amplitude up to the level of a next step.

The patient's tolerance for an increase in a titrated parameter may vary depending on the patient's state, e.g., the patient's level of consciousness, level of attention, mood, general health, gender, age, etc. Changes in the titration process may be made accordingly. For example, if the patient is more tolerant of the increase at night, a current setting may be increased at night (e.g., while the patient is asleep) from a lower amplitude to a higher amplitude. Upon awakening, the amplitude may be maintained at the higher amplitude or reduced to an intermediate value if the patient does not tolerate the higher amplitude when awake. In this manner, the titrating function may accelerate the patient's accommodation to the higher amplitude and/or accelerate the overall titration process.

Figure 6:
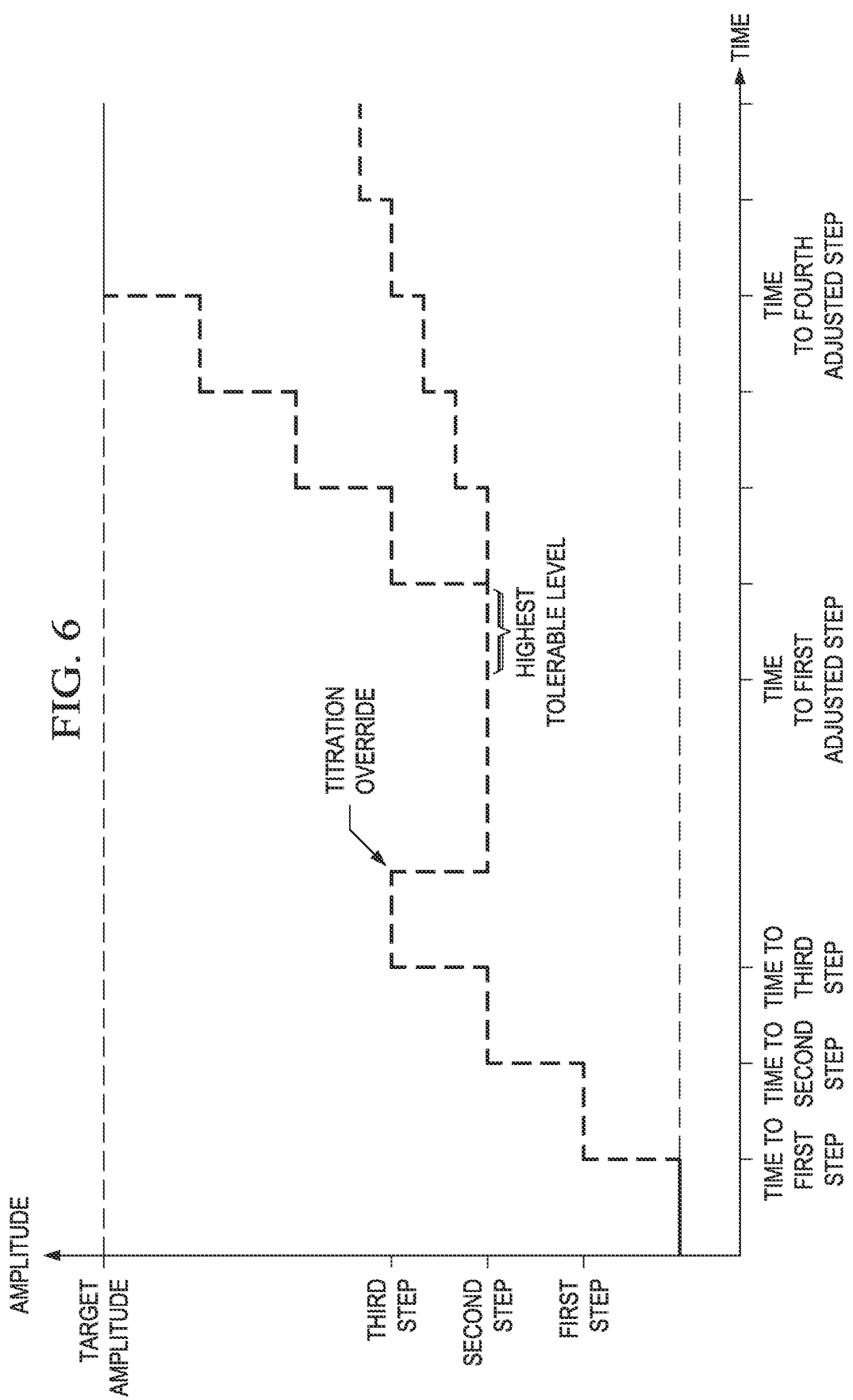
FIG. 6 shows examples of a titration of a first electrical parameter involving a dynamic adjustment to a programmed titration, according to some embodiments of the present disclosure.

FIG. 6 illustrates a stylized depiction of one example of a dynamic adjustment of a titration function, according to some embodiments. Again, by way of example, the depicted value along the y-axis of FIG. 6 is the first electrical therapy parameter, e.g., current amplitude. The general principles illustrated, however, are applicable to any electrical therapy parameter that may be titrated as part of a therapy titration to an efficacious dosage. In this example, an adverse effect (not shown) is determined to occur sometime after titrating up to the $3^{rd}$ step. As shown, the dynamic adjustment comprises reducing the value of the first parameter, e.g., current amplitude, to the last known tolerable value (e.g., the value of the $2^{nd}$ step), lengthening of the duration of the current tolerable/safe magnitude before the first parameter is titrated to the next higher magnitude. In one embodiment, subsequent steps may be initiated at the originally programmed step magnitude, as illustrated by the series of steps leading to the target value (dashed line), while in alternative embodiments, the dynamic adjustment may also or alternatively comprise decreasing the step magnitude to be applied at future titration steps, as shown by the adjusted steps having a smaller magnitude than the earlier ($1^{st}$, $2^{nd}$ and $3^{rd}$) step magnitudes (dotted line).

In embodiments having a reduced step magnitude, a new (greater) titration time period for reaching the target value may be determined. That is, upon detection of an adverse event, the titration step magnitude may be reduced for future titration steps resulting in a longer titration time period necessary to reach the target value for the electrical therapy parameter(s) being titrated. In this manner, a more comfortable and/or safer titration process may be provided to the patient.

Figure 7:
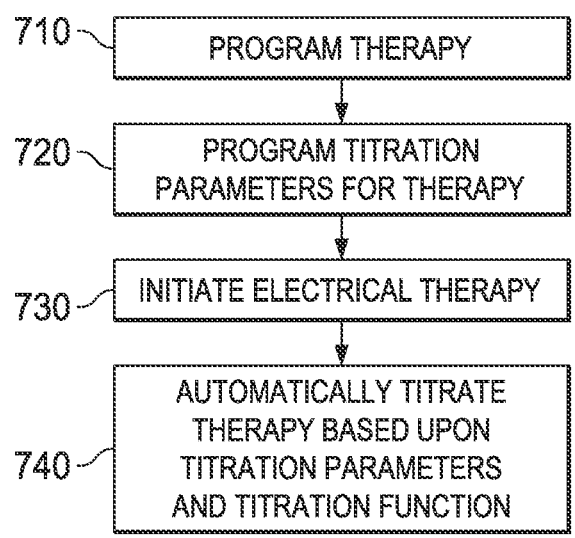
FIG. 7 shows a flowchart depiction of a method, according to some embodiments of the present disclosure.

FIG. 7 illustrates a flowchart representation of a method 700 for performing an automated titration of one or more electrical therapy parameters in accordance with some embodiments herein. Parameters defining an electrical therapy may be programmed (block 710) into a medical device based upon at least one target value for an electrical parameter to be titrated (e.g., an electrical therapy that the patient cannot immediately tolerate at the dosage associated with the target value). The therapy regimen may be configured to treat one or more of several diseases, such as epilepsy, depression, pain, congestive heart failure, traumatic brain injury, or obesity.

Programming at 710 may include providing first value(s) and target value(s) for at least one parameter.

One or more titration parameters characterizing the titration of the one or more electrical therapy parameters being titrated may be programmed into the medical device (block 720). The electrical therapy may be implemented with the electrical therapy parameters to be titrated having their first or initial values (block 730). Thereafter, the electrical therapy may be automatically titrated (block 740) based on the programmed target value(s) of the electrical parameter(s), the titration parameters, and a titration function. The titration function may include various patterns for adjusting the electrical therapy parameter(s), e.g., uniform titration magnitude steps and titration step intervals, or non-uniform adjustments (e.g., according to a parabolic function, a higher-order polynomial, etc.).

In some embodiments, the method 700 may further comprise sending a message to the patient and/or a caregiver or healthcare provided a physician when the target value is reached, or when a change to the programmed titration has occurred, or when a side effect has been detected.

Figure 8:
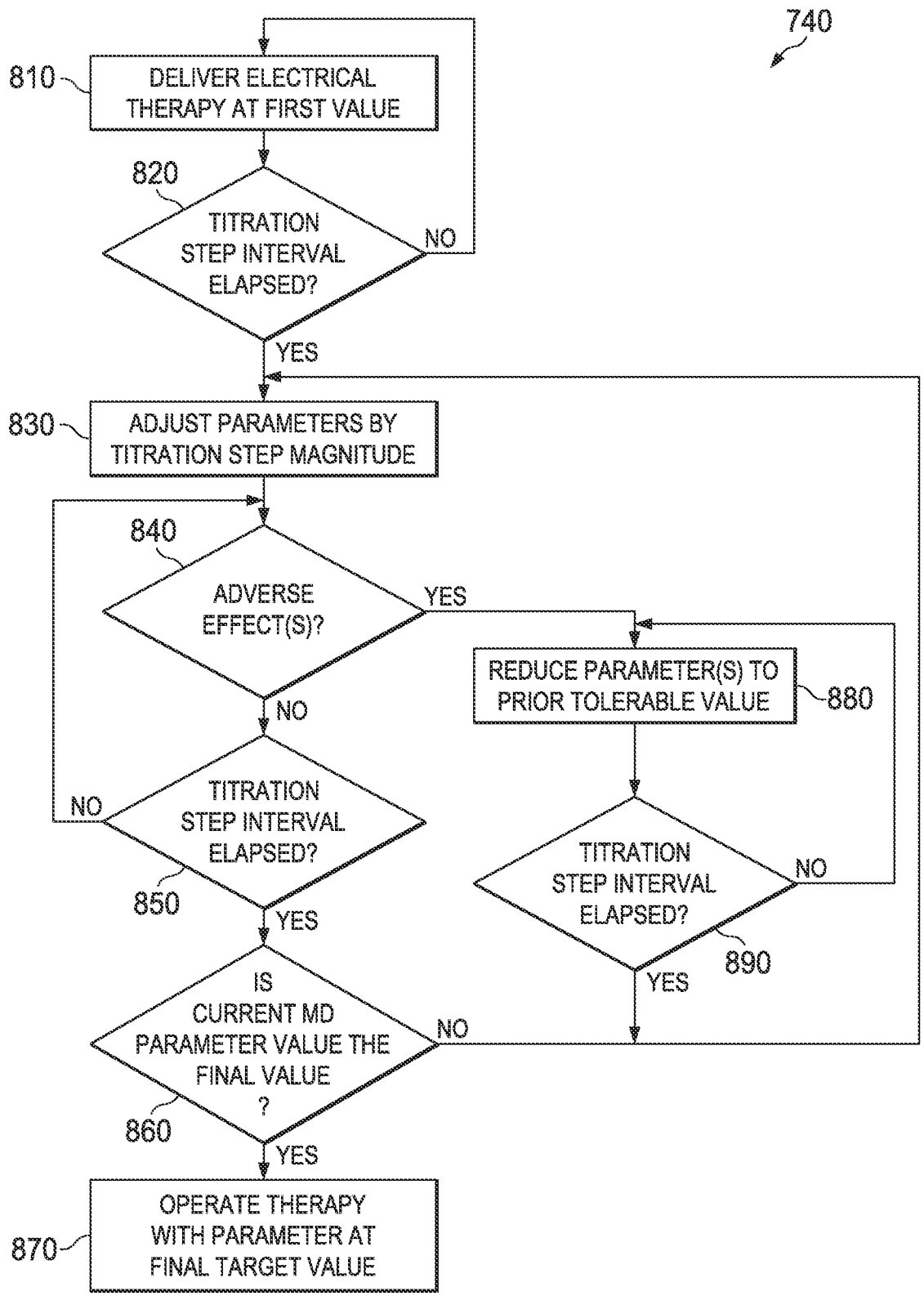
FIG. 8 shows a flowchart depiction of a method, according to some embodiments of the present disclosure.

FIG. 8 illustrates a flowchart depiction of automatically titrating the electrical therapy based upon the titration parameters and the titration function (block 740 of FIG. 7), in accordance with some embodiments herein. At block 810, the medical device 100 may deliver the therapy at the first (initial) values for the electrical therapy parameters programmed into the medical device.

As the therapy is delivered, logic in the MD 100 determines whether or not the titration step interval has elapsed (block 820). If so, the electrical therapy parameter(s) to be titrated are adjusted by the titration step magnitude (block 830).

In one embodiment, titration logic in the MD 100 determines whether or not an adverse effect has occurred (block 840). If no adverse event has occurred, the logic thereafter checks to determine if the next titration step interval has elapsed (block 850). If the titration step interval has not elapsed, the logic continues to check for adverse effects (block 840), and if the titration step interval has elapsed, the logic checks to determine if current value of the electrical signal parameter is the final value (block 860). If the current value is the final value, MD 100 continues to operate the therapy with the parameter at the target value (block 870), while if the final titration value has not been reached, the logic again adjusts the electrical therapy by the titration step magnitude (830).

If at any point after an adjustment is made (block 830) an adverse effect occurs (block 840), the value of the electrical therapy parameter is reduced to a prior tolerable value (block 880), e.g., a highest previously tolerable amplitude. In some embodiments, changes to one or more of the titration step magnitude and the titration step interval may also be made as part of block 880. In alternative embodiments, the therapy may be suspended rather than continued at a reduced stimulation dosage. After the reduction of the electrical therapy parameter to a lower value (with or without changes to the step magnitude and/or interval), the logic then checks to determine if the titration step interval has elapsed (either as originally programmed or as modified) at step 890. If the interval has elapsed, the electrical therapy parameter is adjusted by the titration step magnitude at step 830.

The indications of an adverse effect or event (840) may be based on one or more body indices derived from a body signal. Exemplary body indices include one or more of the patient's heart rate, heart rate variability, blood oxygen saturation, respiratory rate, blood oxygen saturation variability, respiratory rate variability, discomfort, shortness of breath, or vocal cord function. Unacceptable changes indicative of a lack of patient tolerance may be used to indicate the occurrence of an adverse effect. Alternatively or in addition, a manual input from the patient or another external source, such as a medical professional, may be used to indicate an adverse effect. Exemplary manual inputs include but are not limited to tap sensor inputs, magnetic sensor inputs, manipulation of one or more physical or virtual keys on a handheld device, etc.

In some embodiments, the adverse event indication may include a severity of the adverse effect, or to the rate of occurrence of an effect that at a low rate would not be an adverse effect. When adverse events occur, the magnitude of the reduction of the electrical signal parameter and/or changes to the titration step interval and step magnitude (block 880) may be based on the type, severity and/or rate of the adverse effect.

In some embodiments, if no adverse effect is determined at block 840 to have occurred, then the current and/or a future second period can be shortened, i.e., the titration of the parameter may take place more rapidly than originally programmed if there are no significant adverse effects.

Figure 9:
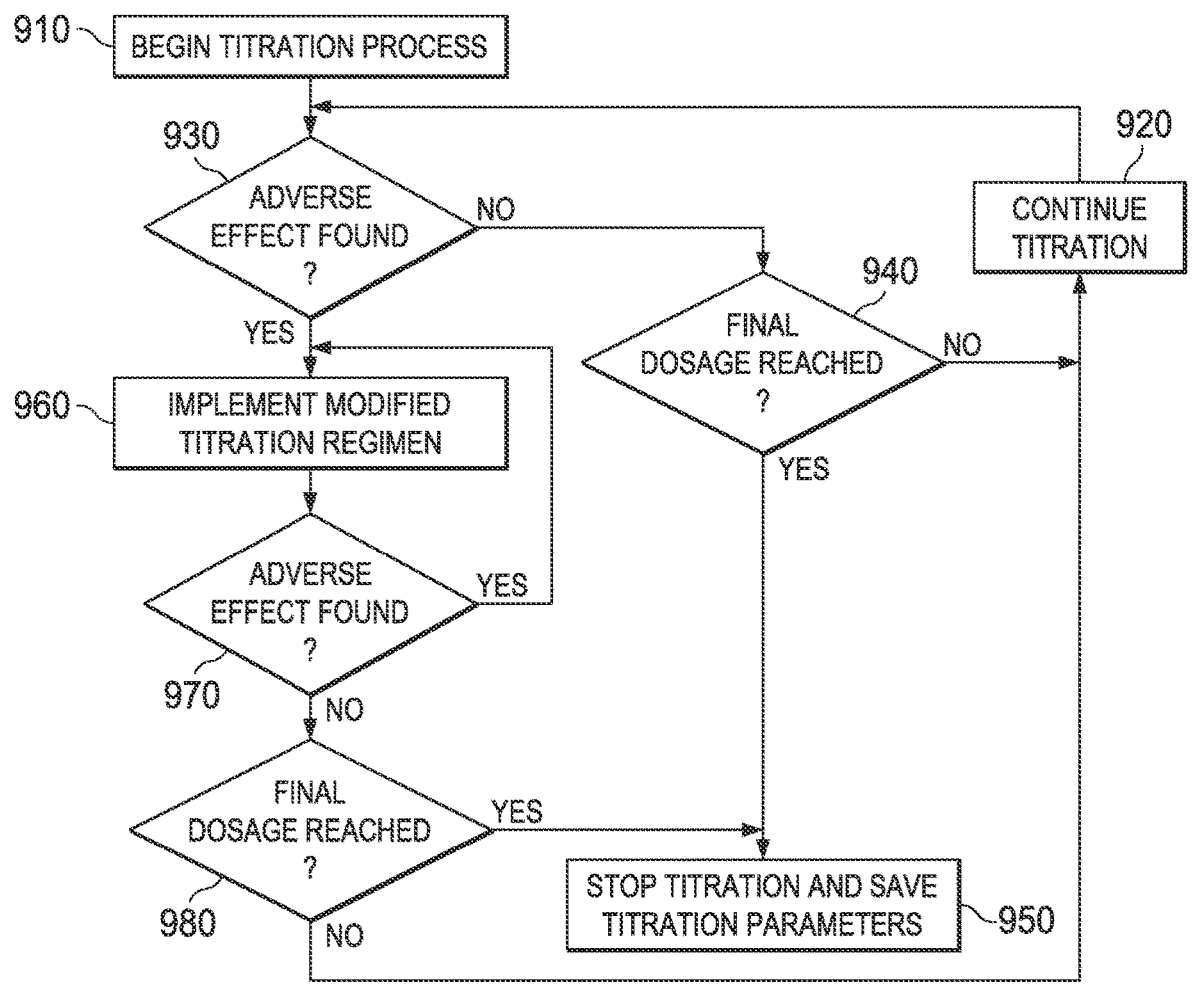
FIG. 9 shows a flowchart depiction of a method for performing a titration process, according to some embodiments of the present disclosure.

Turning to FIG. 9, a simplified flowchart diagram for performing a titration process in accordance with some embodiments herein is illustrated. A dosage for providing a therapy may be determined, and based upon the dosage, a titration regimen may be initiated (block 910). In some embodiments, the titration regimen is based upon the dosage and/or one or more specific characteristics of the patient, e.g., patient tolerance level.

Upon performing one or more upward titration steps, one or more body data may be received and analyzed to determine whether there exists an adverse effect (block 930). In other embodiments, an external source may provide the medical device 100 an indication of an adverse effect. For example, the patient may provide a manual input that is indicative of an adverse effect. In other embodiment, the medical device 100 may receive a signal from an external device, indicating an adverse effect.

Upon a determination that no adverse effect has been found (block 930), the medical device may determine whether the final dosage has been reached (block 940). If the final dosage has been reached, the medical device may stop the titration process and save the titration parameters (block 950). Upon a determination that the final dosage has not been reached (block 940), the medical device may continue the titration process (block 920), e.g., by implementing a next titration step upon the passage of a titration step interval. The process may continue as previously discussed (e.g., by returning to block 930).

If the medical device 100 determines that at least one adverse effect has been found (block 930), the medical device 100 may implement a modification of the titration regimen (block 960). This modification may be automatically performed based upon the type of adverse effects detected. Alternatively, or in addition, manual input from a person, or automated input based upon body data, may also affect modification of the titration regimen.

Upon implementing the modified titration regimen, the medical device 100 may again determine whether an adverse effect has been found (block 970). If an adverse effect is found, the medical device 100 may again implement a modification of the titration regimen (as indicated by the path from block 970 to 960). If an adverse effect is not found (block 970) and the final dosage has been reached (block 980), the titration process is terminated and the titration parameters are saved (block 950). If the final dosage has not been reached (block 980), the medical device 100 may continue the titration process, moving the titration in the direction of the final dosage (see path from block 980 to 920). In this manner, an automated and/or manual implementation of a titration regimen, moving upwardly towards the therapy dosage, is implemented while reducing the risk of adverse effects.

Figure 10:
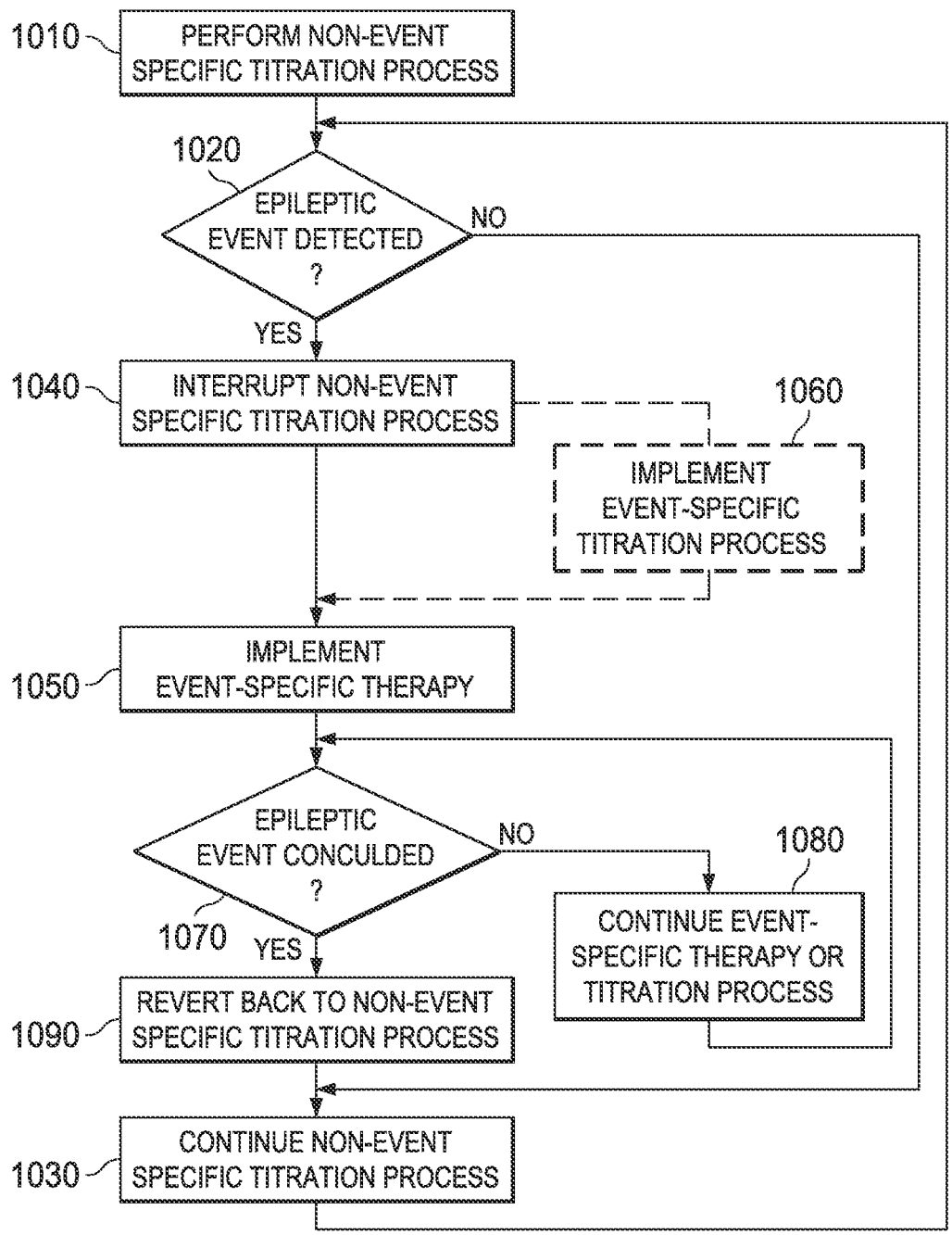
FIG. 10 shows a flowchart depiction of a method for implementing a titration interrupt and/or a multi-titration process, according to some embodiments of the present disclosure.

Turning now to FIG. 10, a flowchart diagram for a method of implementing a titration interrupt and/or a multi-titration process, in accordance with some embodiments is illustrated. Upon determining a dosage for therapeutic treatment stimulation for a disease such as epilepsy, a non-event-specific state titration process may be initiated (block 1010). The non-event-specific state titration process is performed to automatically initiate a treatment regimen, to gradually reach a full dosage regimen to treat a condition (e.g., epilepsy). The non-event-specific state titration is performed at pre-programmed times and in pre-programmed steps independent of the occurrence of seizures, (e.g., open-loop process). That is, in some embodiments, the non-event-specific state titration process may be not responsive to a particular epileptic event. In one embodiment, the non-event-specific state titration process may be implemented in the manner described in FIG. 9.

Continuing referring to FIG. 10, the medical device 100 may continuously check to determine whether an epileptic event (e.g., a seizure, a fall associated with a seizure, an accident associated with a seizure, etc.) is detected (block 1020). If no epileptic events are detected, the non-event-specific state titration process is continued (block 1030). If and when an epileptic seizure is detected, the non-event-specific state titration process may be temporarily interrupted (block 1040). Upon interrupting the non-event-specific state titration process, in one embodiment, the medical device 100 may implement an event-specific therapy (block 1050) (e.g., closed-loop). The event-specific therapy may be a specific therapy regimen that is directed to treat the specific type of event (e.g., seizure) that is detected. For example a 1st therapy signal may be provided for a clinical seizure, while 2nd therapy may be provided for a sub-clinical seizure. In other embodiment, a 1st therapy signal may be provided for a generalized seizure, while a 2nd therapy signal may be provided for a partial seizure. In yet other embodiments, other distinctions for seizures (e.g., simple partial or complex partial or secondarily generalized seizure etc.) may be used to implement specific therapy signals tailored to address those distinctions. In some embodiment, a look-up function may be performed to select the various parameters (e.g., frequency, pulse-train parameters, pulse-width, inter-pulse interval, amplitude, etc.) relating to the therapy signal. The event-specific therapy/titration process may be closed-loop process, specific to the treatment of the epileptic event, wherein this process terminates with the epileptic event.

In an alternative embodiment, upon interrupting the non-event-specific state titration process (block 1040), an event-specific titration process may be implemented (block 1060). The event-specific titration process may provide for determining a dosage to treat the specific epileptic event that has been detected, and initiate a treatment regimen using parameter settings that are increased to a full-dosage setting to treat the epileptic event. Upon implementing the event-specific (e.g., closed-loop) titration process, the medical device 100 may then implement an event-specific therapy based upon the event-specific titration. In one embodiment, the time-periods relating to the step-wise increases in one or more parameters associated with the event-specific titration process are equal to or larger than those relating to the non-event-specific state titration process. The event-specific therapy/titration process may be closed-loop process, specific to the treatment of the detected epileptic event, wherein this process terminates with the epileptic event.

Upon performing either of the two processes of blocks 1040 and 1060 (event-specific therapy or event-specific titration), the medical device 100 may determine whether the epileptic event had concluded or sufficiently subsided (block 1070). Upon a determination the epileptic event has not sufficiently subsided, the event-specific therapy or event-specific titration is continued (block 1080). Upon a determination the epileptic event has concluded or has sufficiently subsided, the medical device 100 may revert back to the non-event-specific state titration process (block 1090).

In some embodiments, the present disclosure may relate to a method of providing a bringing an electrical stimulation regimen administered by a medical device to a target dosage, comprising programing a therapy regimen based upon at least one target electrical parameter; programming one or more titration parameters for titrating to the target electrical parameter; initiating the electrical therapy at the programmed initial values; receiving a body signal after initiating the therapy at the programmed initial values; determining whether there is an adverse effect associated with the therapy, based upon the body signal; adjusting one or more titration parameters to yield an adjusted titration, in response to a determining that there is an adverse effect associated with the therapy; implementing the adjusted titration, and titrating the at least one target electrical parameter according to the adjusted titration.

Receiving the body signal may comprise receiving at least one of autonomic data, neurological data, endocrine data, metabolic data, tissue stress marker data, responsiveness data, or physical fitness data.

Adjusting may comprise returning the electrical parameter value to a prior value. The adjusted therapy may be safe, efficacious, and/or tolerable.

This method may further comprise alerting a physician, in response to a cardiac or respiratory adverse effect.

This method may further comprise determining an efficacy of the adjusted therapy. This method may further comprise stopping the titration process and notifying a physician, in response to the adjusted therapy being efficacious before the target parameter is reached.

In some embodiments, the target electrical parameter may be selected from an amplitude, a pulse width, a pulse frequency, a signal on-time, a waveform, a level or degree of charge balance in a pulse, a polarity, a signal off-time, or two or more thereof. For example, adjusting the therapy may comprise at least one of reducing an electrical current amplitude of the electrical parameter, or determining a modified titration function.

In some embodiments, increasing the electrical parameter value may be performed during states in which taking said step is most comfortable or safe. For a therapy such as vagus nerve stimulation that may cause throat discomfort or coughing, increasing the electrical parameter may be performed while the patient is asleep when the discomfort or pain thresholds are higher than during wakefulness. In some embodiments, the titration may comprise detecting a patient state, where the patient state is one or more of sleeping, awake, resting awake, sitting and awake, active and awake, and exercising. Detecting whether the patient is sleeping may further comprise detecting a sleep state of the patient selected from stage 1, stage 2, stage 3, stage 4, and REM sleep, light sleep, and deep sleep. In some embodiments, where the electrical therapy may use bradycardia, increasing the electrical parameter value may take place only while the patient is awake to minimize the risk of not detecting symptoms associated with the slowing down of the patient's heart rate.

The electrical stimulation regimen of this method may be configured to treat epilepsy, depression, pain, congestive heart failure, traumatic brain injury, or obesity.

In any of the automatic titration methods described herein, the titration may be suspended at any step upon the detection of an acute manifestation of the patient's illness, e.g., a seizure if the patient suffers epilepsy, and an alternative, closed-loop therapy to treat the acute manifestation may be implemented. (The acute therapy may involve a second titration process. Further, the second titration process may be implemented by a function that uses as input(s) information regarding the first titration process). Upon termination of the acute manifestation, the titration may be resumed, typically at the step at which it was suspended. In some embodiments, however, the titration may be resumed at a higher or lower step.

In some embodiments, a method is provided for performing an interruption of a non-event specific titration process (e.g., open-loop) performed by an implanted medical device, comprising: a) programming the medical device to provide an electrical therapy, wherein the programmed electrical therapy comprises a first target value for a first electrical therapy parameter defining the electrical therapy; b) programming at least one titration parameter for automatically adjusting the first electrical therapy parameter from a first value to the first target value over a titration time period of at least two days, wherein the at least one titration parameter is selected from the titration time period, a titration step interval, a titration step magnitude, and a titration step rate; initiating the electrical therapy, wherein the first electrical therapy parameter comprises said first value; c) automatically titrating the electrical therapy by making a plurality of adjustments to the value of the first electrical therapy parameter, whereby the first electrical therapy parameter is changed from the first value to a second target value according to a titration function; d) detecting an epileptic event; e) interrupting the open-loop titrating process in response to detecting an epileptic event; f) providing an event-specific (e.g., closed-loop) therapy; and g) reverting back to the non-event specific titration process in response to a determination that the epileptic event has concluded.

In other embodiments, a method is provided for performing an interruption of a non-event specific titration process performed by an implanted medical device, comprising: a) performing a non-event specific titration process; b) detecting an epileptic event; c) interrupting the non-event specific titration process in response to detection the epileptic event; d) implementing an event-specific titration process for delivering a therapy in response the detection of the epileptic event; and e) reverting back to the non-event specific titration process in response to a determination that the epileptic event has concluded.

In yet another embodiment, a method is provided for modifying a titration process for providing a therapy by a medical device (fully implanted, partially implanted or external to the patient) comprising: a) initiating a titration process to treat a chronic condition, wherein the titration process includes programming at least one titration parameter for automatically adjusting an electrical therapy parameter from a first value to the first target value over a titration time period; b) determining whether an adverse effect resulting from the titration has been found; c) modifying at least one parameter associated with the titration process; and d) implementing a modified titration process. In some embodiments, the titration process and/or the modified titration process is continued upon determining that a final dosage of the therapy had been reached.

The methods described above may be implemented by the medical device 100 and/or the medical device system 150. The methods described above may be governed by instructions that are stored in a non-transitory computer readable storage medium and that are executed by, e.g., a processor 217 of the medical device 100.

The methods depicted in FIGS. 7-10 and/or described above may be governed by instructions that are stored in a non-transitory computer readable storage medium and that are executed by, e.g., a processor 217 of the medical device 100. Each of the operations shown in FIGS. 7-10 and/or described above may correspond to instructions stored in a non-transitory computer memory or computer readable storage medium. In various embodiments, the non-transitory computer readable storage medium includes a magnetic or optical disk storage device, solid state storage devices such as flash memory, or other non-volatile memory device or devices. The computer readable instructions stored on the non-transitory computer readable storage medium may be in source code, assembly language code, object code, or other instruction format that is interpreted and/or executable by one or more processors.

What is claimed:

1. A method of automatically titrating an electrical therapy administered to a patient by an implanted medical device, the method comprising:
    initiating via the implanted medical device the electrical therapy;
    automatically titrating the electrical therapy by making a plurality of adjustments to a value of at least a first electrical therapy parameter via a titration parameter, whereby the first electrical therapy parameter is changed from a first value to a first target value;
    receiving body signals after an initiation of at least one of the plurality of adjustments to the value of the first electrical therapy parameter;
    determining an occurrence of an epileptic event based on a first body signal;
    interrupting the automatic titration of the electrical therapy based on the determination of the occurrence of the epileptic event where the electrical therapy had an interrupted automatic titration value at an interruption time;
    initiating an epileptic event therapy;
    determining that the occurrence of the epileptic event has concluded based on a second body signal;
    automatically returning to the interrupted automatic titration value of the first electrical therapy parameter, in response to determining that the occurrence of the epileptic event has concluded;
    continuing the titration procedure from the interrupted automatic titration value of the electrical therapy;
    receiving a third body signal indicating that the electrical therapy has caused an adverse effect;
    interrupting the titration procedure based on the adverse effect; and
    reinitiating the automatically titrating the electrical therapy by making the plurality of adjustments to a current value of the first electrical therapy parameter to change the current value to the target value based on the adverse effect.

2. The method of claim 1, further comprising modifying a titration function in response to reinitiating the automatically titrating the electrical therapy, and wherein automatically titrating the electrical therapy comprises making at least one adjustment to the value of the first electrical therapy parameter to adjust the value of the first electrical therapy parameter to the first target value according to the modified titration function.

3. The method of claim 1, wherein the electrical therapy is configured to treat a medical condition selected from epilepsy, depression, obesity, bulimia, traumatic brain injury, heart failure, stroke, coma, fibromyalgia, addiction disorders, multiple sclerosis, hearing disorders, dementia, sleep disorders, pain, migraine, pancreatic disorders, diabetes, hypertension, heart failure, angina, and syncope.

4. The method of claim 1, wherein receiving the first body signal, the second body signal, and the third body signal comprises receiving at least one of autonomic data, neurological data, endocrine data, metabolic data, tissue stress marker data, responsiveness data, or physical fitness data.

5. A medical device system for providing an electrical therapy, comprising:
    a programmer for programming an implantable medical device with an electrical therapy, wherein the programmer enables a user to program into the implantable medical device:
        a first value for a first electrical therapy parameter,
        a first target value for the first electrical therapy parameter, and
        at least one titration parameter for automatically adjusting the first electrical therapy parameter from the first value to the first target value;
    an electrode configured to deliver the electrical therapy;
    a body data module capable of receiving body signals from the patient;
    the implantable medical device, comprising:
        an electrical therapy module to provide the electrical therapy to the patient using the electrode; and
        a therapy titration module configured to automatically titrate via a titration procedure the electrical therapy by making a plurality of adjustments to a value of the first electrical therapy parameter, whereby the first electrical therapy parameter is changed from the first value to the first target value according to a titration function;
    the implantable medical device configured to: determine an occurrence of an epileptic event based on a first body signal; interrupt the automatic titration of the electrical therapy based on the determination of the occurrence of the epileptic event where the electrical therapy had an interrupted automatic titration value at an interruption time; initiate an epileptic event therapy; determine that the occurrence of the epileptic event has concluded based on a second body signal; automatically return the interrupted automatic titration value of the first electrical therapy parameter, in response to determining that the occurrence of the epileptic event has concluded;
    the implantable medical device configured to: continue the titration procedure from the interrupted automatic titration value of the electrical therapy; receive a third body signal indicating that the electrical therapy has caused an adverse effect; interrupt the titration procedure based on the adverse effect; and reinitiate the automatically titrating the electrical therapy by making the plurality of adjustments to a current value of the first electrical therapy parameter to change the current value to the target value based on the adverse effect.

6. The medical device system of claim 5,
    wherein the therapy titration module comprises a dynamic adjustment unit configured to accelerate, slow down, suspend, or resume the titration procedure based on body data received from the patient.

* * * * *